US008726944B2

(12) United States Patent
Carlsson et al.

(10) Patent No.: US 8,726,944 B2
(45) Date of Patent: May 20, 2014

(54) POSITIONING OF DISPENSING MEANS IN FRACTION COLLECTOR

(75) Inventors: Johan L. Carlsson, Kungsangen (SE); Hakan Frojdh, Uppsala (SE); Pia Liljedahl, Uppsala (SE); Lars Rosengren, Uppsala (SE); Johan Svensson, Uppsala (SE); S. Fredrik Svensson, Jarfalla (SE); Bengt Asberg, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 769 days.

(21) Appl. No.: 12/988,946

(22) PCT Filed: Apr. 22, 2009

(86) PCT No.: PCT/SE2009/050417
§ 371 (c)(1),
(2), (4) Date: Oct. 21, 2010

(87) PCT Pub. No.: WO2009/131534
PCT Pub. Date: Oct. 29, 2009

(65) Prior Publication Data
US 2011/0036450 A1 Feb. 17, 2011

(30) Foreign Application Priority Data
Apr. 23, 2008 (SE) ........................ 0800932

(51) Int. Cl.
*G01N 35/10* (2006.01)
(52) U.S. Cl.
CPC ................ *G01N 35/1011* (2013.01)
USPC ............. 141/1; 141/130; 141/156; 422/63; 422/65; 422/67; 422/400; 436/180; 73/863.01

(58) Field of Classification Search
CPC ..................................... G01N 35/1011
USPC ............. 141/1, 129, 130, 156, 250-284, 94; 422/63, 65, 67, 68.1, 501, 502, 509, 422/521, 552, 561; 436/180; 356/244; 435/288.4
See application file for complete search history.

(56) References Cited

U.S. PATENT DOCUMENTS

| | | | | | |
|---|---|---|---|---|---|
| 4,159,875 | A | * | 7/1979 | Hauser | 356/244 |
| 4,166,483 | A | * | 9/1979 | Nordlund | 141/1 |
| 4,431,924 | A | * | 2/1984 | Suovaniemi et al. | 250/566 |
| 4,757,437 | A | * | 7/1988 | Nishimura | 700/64 |
| 5,416,329 | A | * | 5/1995 | Sonne et al. | 250/364 |
| 5,460,057 | A | * | 10/1995 | Ostrup | 73/864.81 |
| 5,592,289 | A | * | 1/1997 | Norris | 356/244 |
| 6,024,920 | A | * | 2/2000 | Cunanan | 422/65 |
| 6,097,025 | A | * | 8/2000 | Modlin et al. | 250/227.22 |
| 6,448,089 | B1 | * | 9/2002 | Vuong | 436/164 |

(Continued)

FOREIGN PATENT DOCUMENTS

RU 2313912 C2 12/2007
WO WO 01/77640 10/2001

*Primary Examiner* — Timothy L Maust
*Assistant Examiner* — Robert Bell, III

(57) ABSTRACT

A method in a fraction collector for accurate positioning of a dispensing device with respect to wells of a micro plate in which prior to the dispensing a sensing device is moved over the micro plate the sensing device being able to detect the number of walls between the wells in the rows and columns of the micro plate.

7 Claims, 4 Drawing Sheets

(56) References Cited

U.S. PATENT DOCUMENTS

| | | | |
|---|---|---|---|
| 6,551,557 B1* | 4/2003 | Rose et al. | 422/502 |
| 6,558,623 B1* | 5/2003 | Ganz et al. | 422/63 |
| 7,235,215 B2* | 6/2007 | Velghe et al. | 422/520 |
| 7,352,889 B2* | 4/2008 | Ganz et al. | 382/141 |
| 7,364,697 B2* | 4/2008 | McFarland et al. | 422/62 |
| 7,371,347 B2* | 5/2008 | Wulf et al. | 422/501 |
| 7,503,356 B2* | 3/2009 | Morikawa | 141/250 |
| 7,585,463 B2* | 9/2009 | Austin et al. | 422/63 |
| 7,629,173 B2* | 12/2009 | Gollier et al. | 436/164 |
| 7,842,246 B2* | 11/2010 | Wohlstadter et al. | 422/401 |
| 7,858,382 B2* | 12/2010 | Kim et al. | 436/164 |
| 2001/0048899 A1* | 12/2001 | Marouiss et al. | 422/100 |
| 2002/0009391 A1* | 1/2002 | Marquiss et al. | 422/63 |
| 2002/0119077 A1 | 8/2002 | Shumate et al. | |
| 2004/0022677 A1 | 2/2004 | Wohlstadter et al. | |
| 2004/0022689 A1 | 2/2004 | Wulf et al. | |
| 2006/0121602 A1* | 6/2006 | Hoshizaki et al. | 435/288.7 |
| 2006/0210435 A1* | 9/2006 | Alavie et al. | 422/65 |
| 2008/0031774 A1* | 2/2008 | Magnant et al. | 422/63 |
| 2010/0092683 A1* | 4/2010 | Ermantraut et al. | 427/424 |
| 2010/0229999 A1* | 9/2010 | Brennan et al. | 141/1 |
| 2013/0280143 A1* | 10/2013 | Zucchelli et al. | 422/501 |

* cited by examiner

POSITIONING OF DISPENSING MEANS IN FRACTION COLLECTOR

CROSS-REFERENCE TO RELATED APPLICATIONS

This application is a filing under 35 U.S.C. §371 and claims priority to international patent application number PCT/SE2009/050417 filed Apr. 22, 2009, published on Oct. 29, 2009 as WO 2009/131534, which claims priority to application number 0800932-6 filed in Sweden on Apr. 23, 2008.

FIELD OF THE INVENTION

The present invention pertains to the field of fraction collectors, particularly to fraction collectors where the receptacles are formed by micro plates.

SUMMARY OF THE INVENTION

A fraction collector is a device used for dispensing a flow of liquid in a number of receptacles where the receptacles are fed towards a dispensing means by means of a relative movement in one or § two directions. As the droplets dispensed can have a diameter of 4 millimeters and the smallest receptacles have an orifice of 6.7 millimeters it is important that the receptacles are held in exactly the right position to avoid spilling. In a fraction collector used e.g. in an HPLC (High Pressure Liquid Chromatography) system it is important that different types of receptacles can be used. Thus the receptacles can consist e.g. of test tubes of various sizes or micro titer plates. This flexibility can be achieved by using a cassette tray onto which various types of cassettes for various types of receptacles can be loaded. The various types of cassettes are provided with some type of identification means so that the fraction collector can read e.g. the size of the test tubes and make the correct positioning of the dispensing means.

However, a problem arises when using micro plates since there are many types of deep well plates all with the same foot print. Thus, even if different types of cassettes were used for different types of plates there is no way to ensure that the user does not use the wrong type of cassette for his plate. Thus there is a need for a method for distinguishing between different types of deep well plates used in the same type of cassette so as to ensure a correct positioning of the dispensing means vis-à-vis the wells.

Thus it is an object of the present invention to provide for a method in a fraction collector where fractions of liquid are sequentially dispensed from a dispensing means into a plurality receptacles by displacing the receptacles relative to the dispensing means, said receptacles being formed by a matrix of wells in a plate, for ensuring a correct positioning of the dispensing means vis-à-vis said wells and a fraction collector for carrying out the method. The characteristics of the invention will appear from the claims enclosed to the specification.

Further scope and applicability of the present invention will become apparent from the detailed description given hereinafter. However it should be understood that a detailed description and specific examples while indicating preferred embodiments of the invention are given by illustrations only. There are changes and modifications in the spirit and scope of the invention which will become apparent to those skilled in the art from the detailed description below.

DETAILED DESCRIPTION OF THE INVENTION

Figure 1:
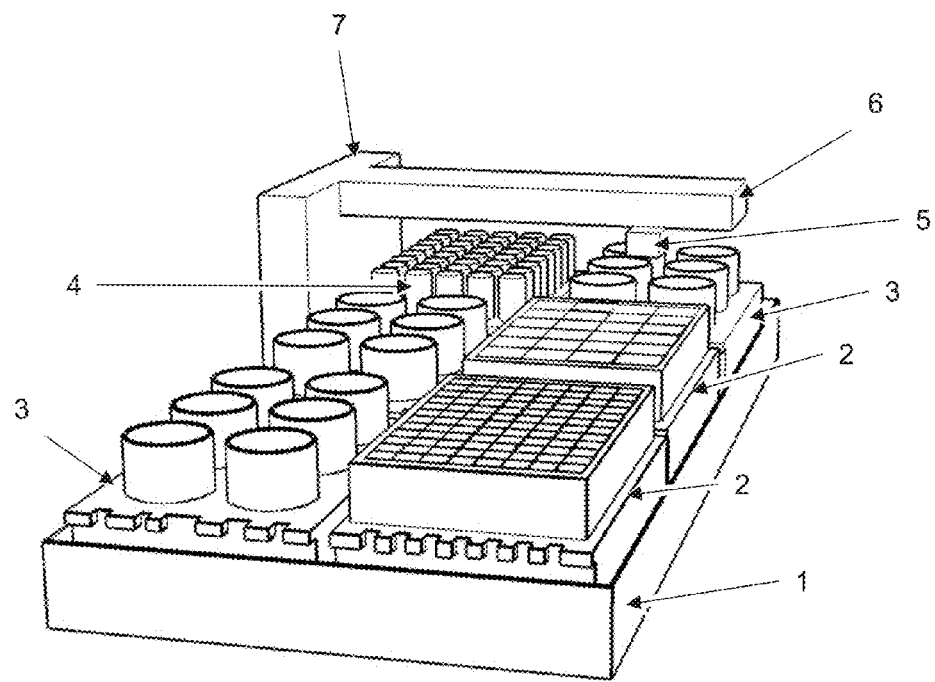
FIG. 1 is a perspective view of a fraction collector in which the method according to the invention is applied.

FIG. 1 shows a schematic perspective view of a fraction collector where the method according to the invention is applied. In the figure reference number 1 denotes a cassette tray onto which are loaded a number of cassettes of different types depending on the type of receptacles they are to hold. Thus reference number 2 denotes cassettes for holding micro titer plates whereas reference numbers 3 and 4 denote cassettes for holding test tubes of different dimensions. The fraction collector is further provided with an arm 6 held by a holder 7 movable in the y-direction. On the arm 6 is arranged a sensing and dispensing head 5 movable in the x-direction. Thus the dispensing head can be moved across all cassettes on the cassette tray. The design and operation of the sensing device incorporated in the dispensing head will be described in more detail in connection with FIGS. 2, 3 and 4.

Figure 2:
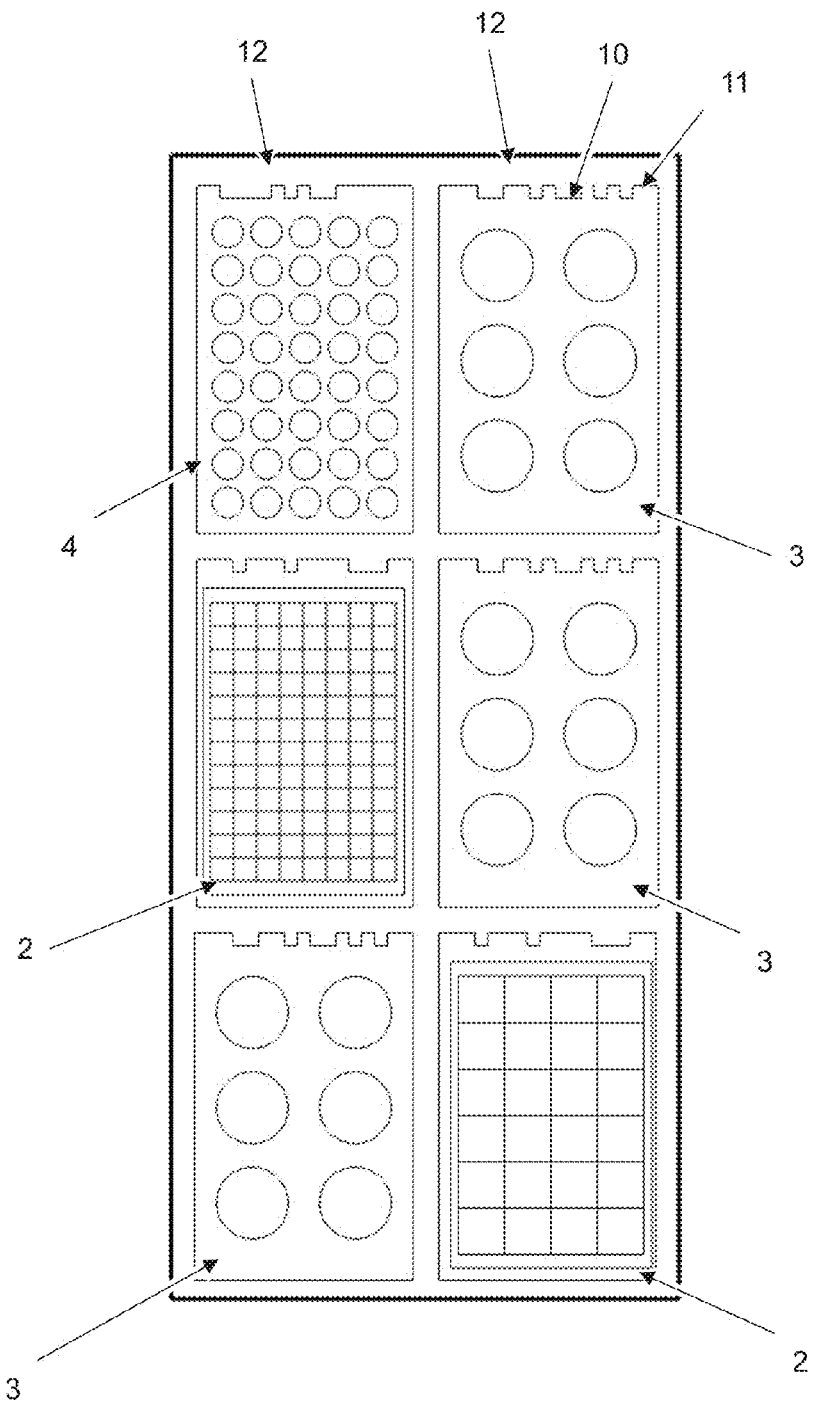
FIG. 2 is a top view of a cassette tray used in the fraction collector of FIG. 1.

In FIG. 2 which shows a top view of a cassette tray as shown in FIG. 1 the identical numerals are used for identical parts. As appears from FIG. 2 the different cassettes are provided with bar codes 12 which are different for different types of cassettes. However, the cassettes for micro titer plates have identical bar codes since the same cassettes are used for all micro titer plates irrespective of the number of wells in the plate.

Figure 3:
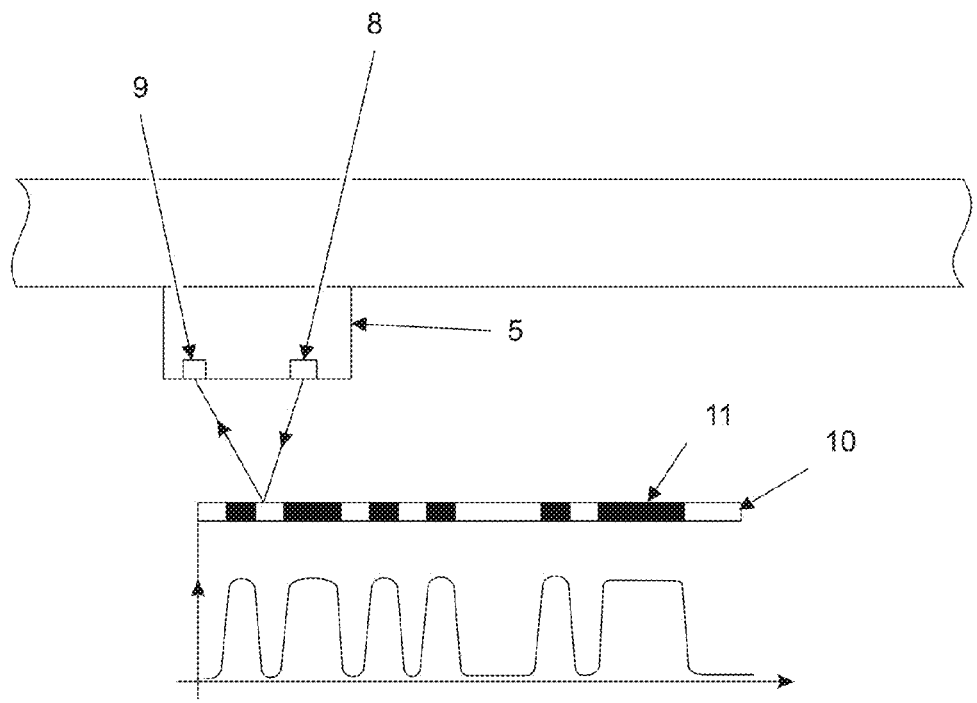
FIG. 3 schematically illustrates the active components in the sensing and dispensing head of the fraction collector of FIG. 1.

FIG. 3 schematically shows the sensing device incorporated in the sense dispensing head 5. The sensing device has two active components, i.e. an infra-red light emitting diode 8 and a spectrally matched detector 9. The LED has a narrow special intensity distribution with a half intensity angle of about 3 degrees. The detector accepts light from a wider angle to reduce aligning efforts. The principle of the device is to detect light scattered from a surface in the active area of the detector. Prior to activating the dispensing process of the fraction collector the head 5 is displaced across the bar codes of the different trays so as to detect the actual type of tray. The aim of the bar code reading algorithm is to decode a sequence of bits into a predefined type of cassette. Each type of cassette is equipped with a bar code consisting of areas that either reflect or absorb light. In this particular case the reflective parts are plastic teeth 11 and the absorbing parts simply areas 10 without any material. Positioning the device over a position with material will cause light from the LED to reach the detector. If no material is present no light will be reflected and thus it will not reach the detector. Moving the device over the bar code will allow the software to identify the barcode pattern as high or low signals from the detector as indicated at the bottom of FIG. 3.

Figure 4:
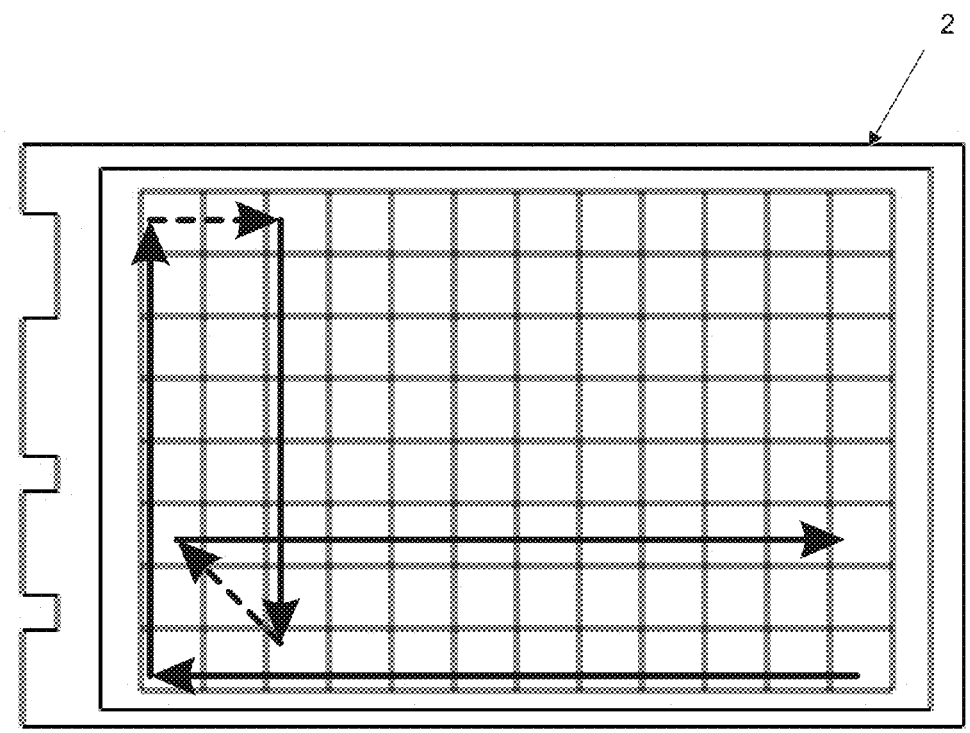
FIG. 4 illustrates a typical reading pattern of the sensing head of FIG. 3.

Thus the sensing device will be able to determine the actual type of tray and generate a signal used to control the movements of the dispensing device. If, however, the sensing device detects a tray for micro plates which could have different numbers of wells this will initiate a scanning of the plate itself preferably according to a pattern as shown in FIG. 4. Thus the device will scan at least one and preferably two rows and columns of the plate and the same type of signal as shown in FIG. 3 will be generated where the walls between the wells will be detected as material and the wells themselves as areas without material. Thus a signal will be generated and stored in the control device of the fraction collector so as to make the dispensing device in the preceding dispensing procedure to make the accurate steps between the wells.

In the same manner as for the bar code reader the device will be used to count the number of wells in a micro titer plate. However, instead of like in the bar code reading case looking for high and low signals the device software will search for peaks in the signal. There are a number of allowed distances between these peaks, each corresponding to a certain well size. By grouping the distances and then checking the most common distance the software determines the size of the well. By doing one sweep in the y-direction and one in the x-direction it is possible to calculate the total number of wells. The software will assume symmetry over the whole plate. The best signal is normally achieved making the code sweep close to the wall. In the center of the well there is a bigger risk for disturbances due to liquid reflections. Since the mechanical tolerance of the systems is too large to ensure one correct sweep this is compensated for by using a dual sweep pattern. Each direction of the plate is swept twice with a predefined offset between the sweeps. The offset is not an integral multiple of the well separation ensuring that at least one of the sweeps be made over a readable area of the plate (FIG. 4).

A possible development of the algorithm is to compare the position of the peak with the theoretical position of the wall for different types of cassettes and only count the peaks matching the wall position within e.g. +/−1 mm for each cassette type. The type of cassette that has the highest quotient between the number of hits and the theoretical number of hits and has the lowest quotient between the number of misses and the total number of walls is then selected as the actual type of cassette.

Since the devices also are supposed to be able to identify partly liquid filled deep well plates a slight tilt is applied with respect to the z-axis to prevent light from reaching too far into the wells.

Thus by applying the method according to the invention is ensured that irrespectively of the number of wells in the micro titer plate used the dispensing unit will always position itself accurately above the wells.

The invention as described above by way of an example could obviously be varied in many ways. E.g. the LED and its detector could be replaced by some other suitable means such as an ultra sound generator/detector or a TV camera and an image analyser. Such variations are not to be regarded as a departure from the spirit and scope of the invention and all such modifications as would be obvious to one skilled in the art are intended to be included in the scope of the following claims.

It is apparent that many modifications and variations of the invention as hereinabove set forth may be made without departing from the spirit and scope thereof. The specific embodiments described are given by way of example only, and the invention is limited only by the terms of the appended claims.

We claim:

1. A method for operating a fraction collector, said method comprising the steps of:
   i) providing a liquid dispenser for dispensing into one or more of a plurality of receptacles each including a matrix of rows and columns of wells in a plate; and providing a sensing device capable of sensing the positions of the wells;
   ii) operating the sensing device to scan at least one of the rows or columns and thereby generating a signal corresponding to the number of wells in the scanned row(s) or column(s);
   iii) sequentially dispensing fractions of liquid from the dispenser into a respective receptacle by displacing said receptacle relative to said dispenser; and
   iv) using said signal for controlling said relative displacement of said dispenser.

2. The method of claim 1, wherein said sensing device is integrated in said dispensing means.

3. The method of claim 1, wherein at least one row and one column of said plate are scanned by said sensing device.

4. The method of claim 1, wherein at least two rows and/or columns are scanned by said sensing device.

5. The method of claim 1, wherein said plate is arranged in a cassette provided with a bar code equally readable by said sensing device.

6. The method of claim 1, wherein said sensing device consists of an IR sender and IR detector.

7. A fraction collector comprising a combined sensing and dispensing head movable in x- and y-directions and a plurality of cassettes arranged in a cassette tray, said cassettes holding micro plates including liquid wells, said sensing and dispensing head being movable to detect the number of wells in the x- and/or y-directions, by moving across said wells, the head further providing a signal corresponding to the number of wells in at least one of said rows or columns and said signal being used for controlling the displacement of said head during dispensing.

* * * * *